United States Patent [19]

Erdmann et al.

[11] 4,073,742
[45] Feb. 14, 1978

[54] CYANO-SUBSTITUTED BIPHENYL COMPOUNDS AND LIQUID CRYSTALLINE DIELECTRICS CONTAINING THE SAME

[75] Inventors: Dietrich Erdmann; Rudolf Eidenschink; Joachim Krause; Ludwig Pohl, all of Darmstadt, Germany

[73] Assignee: Merck Patent Gesellschaft mit beschrankter Haftung, Darmstadt, Germany

[21] Appl. No.: 781,276

[22] Filed: Mar. 25, 1977

[30] Foreign Application Priority Data

Mar. 29, 1976 Germany .............................. 2613293

[51] Int. Cl.$^2$ ................ C09K 3/34; G02F 1/13; C07C 121/60; C07C 121/64
[52] U.S. Cl. .................... 252/299; 260/465 D; 350/350
[58] Field of Search .......... 260/465 D, 465 F, 465 R, 260/471 R, 473 R; 252/299; 350/160 LC

[56] References Cited

U.S. PATENT DOCUMENTS

| | | | |
|---|---|---|---|
| 3,772,389 | 11/1973 | Lowrance, Jr. ................. | 260/465 D |
| 3,925,238 | 12/1975 | Gavrilovic ............................ | 252/299 |
| 3,947,375 | 3/1976 | Gray et al. ............................ | 252/299 |
| 3,951,846 | 4/1976 | Gavrilovic ............................ | 252/299 |
| 3,952,046 | 4/1976 | Scherrer et al. ..................... | 260/463 |
| 3,953,491 | 4/1976 | Steinstrasser et al. .......... | 260/465 D |
| 3,971,824 | 7/1976 | Van Meter et al. ............. | 260/473 R |
| 4,017,416 | 4/1977 | Inukai et al. ........................ | 252/299 |
| 4,029,594 | 6/1977 | Gavrilovic et al. ................ | 252/299 |
| 4,035,056 | 7/1977 | Coates et al. ........................ | 252/299 |

FOREIGN PATENT DOCUMENTS

| | | | |
|---|---|---|---|
| 2,600,558 | 7/1975 | Germany ............................ | 252/299 |
| 2,348,193 | 4/1974 | Germany ............................ | 252/299 |

OTHER PUBLICATIONS

Liquid Crystals & Plastic Crystals, vol. 1, Gray, G.W., et al., John Wiley & Sons, Inc., N.Y., pp. 103-152, (1974).

Primary Examiner—Benjamin R. Padgett
Assistant Examiner—T. S. Gron
Attorney, Agent, or Firm—Millen & White

[57] ABSTRACT

Biphenyl derivatives of the formula:

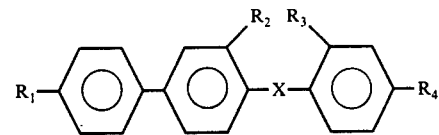

wherein X is —CO—O— or —O—CO—, $R_1$ and $R_4$ are alkyl of 1 to 10 carbon atoms, and one of $R_2$ and $R_3$ is CN and the other is H, are useful for lowering the dielectric anisotropy of liquid crystalline dielectrics.

10 Claims, No Drawings

CYANO-SUBSTITUTED BIPHENYL COMPOUNDS AND LIQUID CRYSTALLINE DIELECTRICS CONTAINING THE SAME

BACKGROUND OF THE INVENTION

The invention relates to cyano-substituted biphenyl compounds and their use for modifying the dielectric anisotropy (DA) of liquid crystalline dielectrics.

Liquid crystalline dielectrics having a clearly negative DA are required for electrooptical display devices, the mode of operation of which is based on the phenomenon of dynamic scattering. Additional requirements to be met by liquid crystalline dielectrics are high chemical stability; a broad temperature range, which includes room temperature, for the nematic phase; and a viscosity as low as possible.

These requirements are only partially satisfied by conventional liquid crystalline dielectric materials of the Schiff base, azoxybenzene, benzoic acid phenyl ester, and thiobenzoic acid phenyl ester types. Schiff bases are chemically unstable, the azoxybenzenes are sensitive to light and UV irradiation, and benzoic acid and thiobenzoic acid phenyl esters are too viscous. Most of the liquid crystalline compounds of these classes of substances have a DA value close to zero.

In order to produce dielectrics having clearly negative DA values, these liquid crystalline compounds can be mixed, for example, with the liquid crystalline compounds of the [2'-cyano- (or 2'-nitro-) -4'-alkyl- (or 4'-alkoxy-)]-phenyl esters of 4-[4-alkyl- (or 4-alkoxy-)benzoyl-oxy]benzoic acid series in accordance with DOS (German Unexamined Laid-Open Application) No. 2,240,864, now U.S. Pat. No. 3,953,491, incorporated herein by reference. These additives all have a high clearing point and, with adequate solubility, can broaden the nematic range of the thus-prepared dielectrics in the desired way.

Unfortunately, however, they also impart to the mixtures high viscosity and accordingly cause undesirably long switching times in electrooptical display devices constructed therefrom.

SUMMARY OF THE INVENTION

In a compositional aspect, this invention relates to novel cyano-substituted biphenyl compounds of Formula I

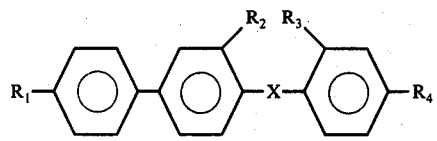

wherein X is —CO—O or —O—CO, $R_1$ and $R_4$ are alkyl of 1–10 carbon atoms, and one of $R_2$ and $R_3$ is H and the other is CN.

In another compositional aspect, this invention relates in a liquid crystalline dielectric composition comprising at least one liquid crystalline compound, to the improvement wherein the composition has a negative dielectric anisotropy by the presence therein of 0.5–40% by weight of a compound of Formula I, provided that the liquid crystalline compound is free of —CN, —NC or —NO$_2$.

This invention further relates to liquid crystal display elements wherein the dielectric composition contains 0.5–40% by weight of a compound of Formula I.

DETAILED DESCRIPTION

Compounds of Formula I are suitable for the modification of liquid crystalline substance to produce dielectrics having clearly negative DA values.

The compounds of this invention are cyano-substituted biphenylcarboxylic acid phenyl esters or benzoic acid biphenylyl esters.

Of these, compounds of Formula Ia and Ib

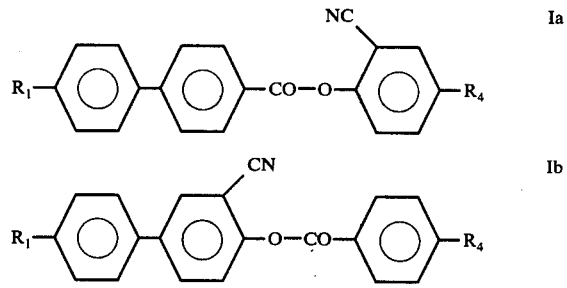

wherein $R_1$ and $R_4$ are alkyl of 1–10 carbon atoms, affect the DA values of liquid crystalline dielectrics produced therewith to a particularly great extent. Therefore, these compounds are preferred.

In compounds of Formula I, the terminal groups $R_1$ and $R_4$ are alike or, preferably, different. Insofar as they are alkyl of three or more carbon atoms, the alkyl can be straight or branched chain. Compounds of general Formula I which exhibit the most advantageous properties are those wherein at least one alkyl is straight-chain, i.e., methyl, ethyl, n-propyl, n-butyl, n-pentyl, n-hexyl, n-heptyl, n-octyl, n-nonyl, or n-decyl. Especially valuable are compounds wherein the two alkyl together contain at least 4, preferably 6–16, most preferably, 8–14 carbon atoms. If a compound of Formula I contains a branched alkyl, the latter preferably has only one branch. In this case, it is especially advantageous if the branching is in the 2- or 3- position, counted from the aromatic nucleus, of the alkyl. The following are preferred branched alkyl: 2-methylpropyl, 2-methylbutyl, 3-methylbutyl, 2-methylpentyl, 3-methylpentyl, 2-methylhexyl, 2-ethylhexyl, 2-methylheptyl, 2-methyloctyl, 2-ethyloctyl, 2-methylnonyl.

Of compounds of Formula Ia, those which are particularly preferred are:
4-n-propylbiphenyl-(4')-carboxylic acid (2-cyano-4-n-pentylphenyl) ester,
4-n-propylbiphenyl-(4')-carboxylic acid (2-cyano-4-n-heptylphenyl) ester,
4-n-pentylbiphenyl-(4')-carboxylic acid (2-cyano-4-n-butylphenyl) ester,
4-n-pentylbiphenyl-(4')-carboxylic acid (2-cyano-4-n-pentylphenyl) ester,
4-n-pentylbiphenyl-(4')-carboxylic acid (2-cyano-4-n-heptylphenyl) ester,
4-n-pentylbiphenyl-(4')-carboxylic acid (2-cyano-4-n-nonylphenyl) ester, and
4-n-heptylbiphenyl-(4')-carboxylic acid (2-cyano-4-n-heptylphenyl) ester.

Of compounds of Formula Ib, those which are particularly preferred are:
4-n-pentylbenzoic acid [3-cyano-4'-n-butylbiphenylyl-(4)] ester, 4-n-pentylbenzoic acid [3-cyano-4'-n-pentylbiphenylyl-(4)] ester,
4-n-pentylbenzoic acid [3-cyano-4'-n-hexylbiphenylyl-(4)] ester,
4-n-pentylbenzoic acid [3-cyano-4'-n-heptylbiphenylyl-(4)] ester,
4-n-hexylbenzoic acid [3-cyano-4'-n-butylbiphenylyl-(4)] ester,
4-n-hexylbenzoic acid [3-cyano-4'-n-pentylbiphenylyl-(4)] ester,
4-n-hexylbenzoic acid [3-cyano-4'-n-hexylbiphenylyl-(4)] ester, and
4-n-butylbenzoic acid [3-cyano-4'-(2-methylpentyl)-biphenylyl-(4)] ester.

Compounds of Formula I are prepared as is customary for such compounds. Preferably, a compound of Formula II

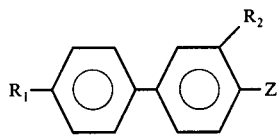

wherein Z is OH, OMe, COOH, or a reactive derivative of the carboxyl, Me is an equivalent of a metal cation, and $R_1$ and $R_2$ are as in Formula I, is reacted at a temperature between $-50°$ and $+250°$ C., optionally in the presence of an organic solvent and/or a customary esterification catalyst, with a compound of Formula III

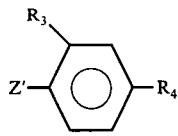

wherein, when Z is OH or OMe, Z' is COOH or a reactive derivative of the carboxyl; and when Z is COOH or a reactive carboxyl derivative, Z' is OH or OMe; and $R_3$ and $R_4$ are as in Formula I.

Suitable reactive carboxyl derivatives for the practice of the invention include —CO-halogen, particularly —COCl; —COO-lower alkyl, e.g. —COOCH$_3$; or an anhydride, such as —COOCOCH$_3$, for example. The OMe are preferably alkali metal or alkaline earth metal phenolate.

The reaction conditions for the process of this invention are determined mainly by the nature of Z and Z'. Thus, a carboxylic acid is normally reacted with a phenol in the presence of a strong acid, for example, a mineral acid, such as hydrochloric or sulfuric acid. A preferred method of conducting the process is to react an acid anhydride or, preferably, an acid chloride with a phenol.

These esterification reactions are preferably effected in an alkaline medium, suitable bases including alkali metal hydroxides, such as sodium or potassium hydroxide; alkali metal carbonates and/or bicarbonates, such as sodium carbonate, sodium bicarbonate, potassium carbonate, or potassium bicarbonate; alkali metal acetates, such as sodium or potassium acetate; alkaline earth metal hydroxides, such as calcium hydroxide; and organic ases, such as triethylamine, pyridine, lutidine, collidine, or quinoline.

The esterification reactions are preferably conducted in an inert solvent. Particularly advantageous solvents are ethers, such as diethyl ether, di-n-butyl ether, tetrahydrofuran, dioxane, or anisole; ketones, such as acetone, butanone, 3-pentanone, or cyclohexanone; amides, such as dimethylformamide or hexamethylphosphoric triamide; hydrocarbons, such as benzene, toluene, or xylene; halogenated hydrocarbons, such as carbon tetrachloride or tetrachloroethylene; and sulfoxides, such as dimethyl sulfoxide or sulfolane. Water-immiscible solvents can be utilized simultaneously and advantageously for removal by azeotropic distillation of water formed during the esterification. Occasionally, an excess of an organic base employed can also be used as solvent for the esterification, e.g., pyridine, quinoline, or triethylamine. In principle, the esterification reactions according to this invention can also be accomplished in the absence of a solvent, for example, by simply heating the components in the presence of sodium acetate.

The reaction temperature ordinarily ranges between $-50°$ and $+250°$ C., preferably between $-20°$ and $+80°$ C. At these temperatures, the esterification reactions are normally terminated after 15 minutes to 48 hours.

Another preferred embodiment of the process of this invention resides in first converting the phenol to be esterified into the sodium or potassium salt thereof, for example, by treatment with ethanolic sodium or potassium hydroxide solution; isolating this salt and suspending same together with sodium bicarbonate or potassium carbonate with stirring in acetone or diethyl ether; and combining this suspension dropwise with stirring with a solution of an acid chloride or anhydride in diethyl ether, acetone, or dimethylformamide. During this process, the reaction mixture is maintained at a temperature between $-25°$ and $+20°$ C., preferably at $-10°$ to $-20°$ C. In this procedure, the esterification reaction is ordinarily finished after 15-50 minutes.

Some of the starting materials for the process of this invention are conventional. Others can be prepared without difficulty following standard procedures of organic chemistry for compounds reported in the literature. For example, 4-alkyl-3'-cyano-4'-hydroxy-biphenyls are obtained by reacting 4-alkyl-4'-hydroxybiphenyls with bromine to obtain 4-alkyl-3'-bromo-4'-hydroxybiphenyls; blocking the hydroxy, e.g., with an acetyl group; replacing bromine by cyano by reaction with copper(I) cyanide in pyridine; and finally removing the blocking group by hydrolysis.

4-Alkyl-3'-cyanobiphenyl-4'-carboxylic acids are prepared from 4-alkyl-4'-amino-3'-bromobiphenyls, which are converted, by diazotization and reaction with copper(I) cyanide, 4-alkyl-3'-bromo-4'-cyanobiphenyl. These products are saponified to 4-alkyl-3'-bromobiphenyl-4'-carboxylic acids, and finally the bromine is replaced by cyano with copper(I) cyanide in pyridine.

4-Alkyl-2-cyanophenols and -benzoic acids can be produced analogously to the biphenyl derivative.

Compounds of this invention normally themselves have a nematic and/or smectic mesophase. However, their melting point is so high, in most cases above 50° C., frequently even above 90° C., that they cannot be utilized alone as liquid crystalline dielectrics for electro-optical display devices intended for operation at room temperature. However, admixture of the compounds of this invention with conventional liquid crystalline substances in amounts of about 0.5–40% by weight, based on the total weight of the mixture, causes, in addition to the desired modification of DA value, a marked lowering of the melting point and an increase in the clearing point. Surprisingly, addition of even relatively large amounts of compounds of this invention increases the viscosity of the dielectric produced only to a minor extent.

Preferably, compounds of this invention are admixed with conventional liquid crystalline dielectric base materials in quantities of 1–35% by weight, most preferably, 5–30% by weight. The amount to be added is determined by the desired DA value or by the solubility of the compound(s) of this invention in the base material.

Suitable base materials for the liquid crystalline dielectrics according to the invention are most of those which have been employed previously for this purpose. These materials can contain, in addition to liquid crystalline compounds, also those which are not liquid crystalline per se, but which are utilized in dielectrics for certain modifications. The most important liquid crystalline compounds used as basic materials of the dielectrics of this invention are of Formula IV

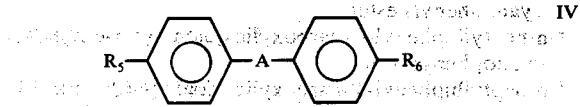

wherein

| A is | —CH=CH— | —CO—S— |
|---|---|---|
| | —CH=CY— | —S—CO— |
| | —CY=CH— | —CH=N— |
| | —C≡C— | —N=CH— |
| | —N=N— | —CH=N(O)— |
| | —N(O)=N— | —N(O)=CH— |
| | —N=N(O)— | or a C—C single bond, |
| | —CO—O— | |
| | —O—CO— | |

Y is halogen, preferably Cl, and $R_5$ and $R_6$, are alkyl, alkoxy, alkanoyl, alkanoyloxy, or alkoxycarbonyloxy of up to 18, preferably up to 8 carbon atoms. In most of these compounds, $R_5$ and $R_6$ are preferably different from each other, one of these being alkyl or alkoxy. A large number of such liquid crystalline compounds is obtainable commercially.

In liquid crystalline compositions of this invention, the base material is selected from those free of —CN, —NC or —NO₂ substituents, that is, compounds of Formula IV wherein $R_5$ and $R_6$ are other than —CN, —NC or —NO₂. It has been found that compounds wherein one of $R_5$ or $R_6$ is —CN, —NC or —NO₂ usually have high positive dielectric anisotropy and are therefore of limited use for preparing materials with clearly negative dielectric anisotropy values.

By additives other than those of Formula I the dielectrics of this invention can be modified so that they can be utilized in all liquid crystal display devices which are presently known. Such additives are known to those skilled in the art and are described in detail in the pertinent literature. It is possible, for example, to add substances for varying the orientation, the conductivity and/or to increase the chemical or photochemical stability. Such materials are described, for example, in DOS No. 2,209,127, and in U.S. Pat. Nos. 3,656,834 and 3,953,491. The possible presence of such materials is encompassed by the above expression of a base material as a component of the dielectrics of this invention.

The liquid crystalline compositions of this invention can be used in a manner known per se in electro-optical display devices utilizing the dynamic scattering effect, and others, such as are described generally and specifically in, e.g., U.S. Pat. Nos. 3,167,107; 3,322,485; 3,499,112; 3,503,672; 3,503,673; 3,532,813; 3,575,491; 3,575,493; 3,592,526; 3,592,527; 3,594,065; 3,597,043; 3,612,654; 3,622,226; 3,625,591; 3,645,604; 3,647,280; 3,654,606; 3,674,338; 3,675,989; 3,690,745; and 3,694,053.

The dielectrics of the present invention are produced in the customary manner. Normally, the desired amount of one or more compounds of Formula I is dissolved in the conventional liquid crystalline substance, suitably at an elevated temperature. By selecting during this step a temperature above the clearing point of the basic material, the completion of the dissolution process can be observed especially easily. However, it is also possible to add to the basic material a solution of the compound of Formula I in a suitable organic solvent, e.g., acetone, chloroform, or methanol, and then to remove the solvent again after thorough mixing, for example, by distillation under reduced pressure. Of course, care must be taken during this operation that no additional, in some cases, undesirable, doping agents are entrained in the mixture by the solvent.

In the physical data, m.p. represents the melting point of a compound, i.e., the conversion temperature of a solid into a liquid crystalline phase, wherein the latter can be smectic or nematic. S./N. means the conversion point of a smectic phase into a nematic phase, and c.p. is the clearing point of the liquid crystalline compound, i.e., the temperature at which a liquid crystalline phase is converted into an isotropic liquid phase, or vice versa.

The temperatures indicated in the examples are in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

During the course of 30 minutes, a solution of 5.5 g. of 4-n-propylbiphenyl-4'-carboxylic acid chloride in 40 ml. of toluene is added dropwise with stirring to a boiling solution of 4 g. of 4-n-pentyl-2-cyanophenol and 5 ml. of pyridine in 40 ml. of toluene. The reaction mixture is refluxed for another 2 hours and then concentrated by evaporation. The residue is combined with 80 ml. of water and extracted three times with 150 ml. portions of diethyl ether. The ether extracts are washed with 200 ml. of water, 150 ml. of 5% sodium bicarbonate solution, and another 200 ml. of water, and dried over sodium sulfate. After the ether has been removed by distillation, the remaining (4-n-pentyl-2-cyanophenyl) ester of 4-n-propylbiphenyl-4'-carboxylic acid is recrystallized from ethanol; m.p. 59°; S./N. 73.5°; c.p. 115°.

Analogously, the following compounds are produced:

4-n-propylbiphenyl-4'-carboxylic acid [4-(2-methylbutyl)-2-cyanophenyl] ester 4-n-propylbiphenyl-4'-carboxylic acid [4-(3-methylbutyl)-2-cyanophenyl] ester 4-n-propylbiphenyl-4'-carboxylic acid (4-n-hexyl-2-cyanophenyl) ester
4-n-propylbiphenyl-4'-carboxylic acid [4-(2-methylpentyl)-2-cyanophenyl] ester
4-n-propylbiphenyl-4'-carboxylic acid [4-(3-methylpentyl)-2-cyanophenyl] ester
4-n-propylbiphenyl-4'-carboxylic acid (4-n-heptyl-2-cyanophenyl) ester, m.p. 59°; S./N. 61.5°; c.p. 104.5°;
4-n-propylbiphenyl-4'-carboxylic acid (4-n-octyl-2-cyanophenyl) ester
4-n-propylbiphenyl-4'-carboxylic acid [4-(2-ethylhexyl)-2-cyanophenyl] ester
4-n-propylbiphenyl-4'-carboxylic acid (4-n-nonyl-2-cyanophenyl) ester
4-n-butylbiphenyl-4'-carboxylic acid (4-n-butyl-2-cyanophenyl) ester
4-n-butylbiphenyl-4'-carboxylic acid [4-(2-methylpropyl)-2-cyanophenyl] ester
4-n-butylbiphenyl-4'-carboxylic acid (4-n-pentyl-2-cyanophenyl) ester
4-n-butylbiphenyl-4'-carboxylic acid [4-(2-methylbutyl)-2-cyanophenyl] ester
4-n-butylbiphenyl-4'-carboxylic acid [4-(3-methylbutyl)-2-cyanophenyl] ester
4-n-butylbiphenyl-4'-carboxylic acid (4-n-hexyl-2-cyanophenyl) ester
4-n-butylbiphenyl-4'-carboxylic acid [4-(2-methylpentyl)-2-cyanophenyl] ester
4-n-butylbiphenyl-4'-carboxylic acid [4-(3-methylpentyl)-2-cyanophenyl] ester
4-n-butylbiphenyl-4'-carboxylic acid (4-n-heptyl-2-cyanophenyl) ester
4-n-butylbiphenyl-4'-carboxylic acid (4-n-octyl-2-cyanophenyl) ester
4-n-butylbiphenyl-4'-carboxylic acid [4-(2-ethylhexyl)-2-cyanophenyl] ester
4-n-butylbiphenyl-4'-carboxylic acid (4-n-nonyl-2-cyanophenyl) ester
4-n-pentylbiphenyl-4'-carboxylic acid (4-n-propyl-2-cyanophenyl) ester
4-n-pentylbiphenyl-4'-carboxylic acid (4-n-butyl-2-cyanophenyl) ester, m.p. 80°; c.p. 97°;
4-n-pentylbiphenyl-4'-carboxylic acid [4-(2-methylpropyl)-2-cyanophenyl] ester
4-n-pentylbiphenyl-4'-carboxylic acid (4-n-pentyl-2-cyanophenyl) ester, m.p. 83°; c.p. 102°;
4-n-pentylbiphenyl-4'-carboxylic acid [4-(2-methylbutyl)-2-cyanophenyl] ester
4-n-pentylbiphenyl-4'-carboxylic acid [4-(3-methylbutyl)-2-cyanophenyl] ester
4-n-pentylbiphenyl-4'-carboxylic acid (4-n-hexyl-2-cyanophenyl) ester
4-n-pentylbiphenyl-4'-carboxylic acid [4-(2-methylpentyl)-2-cyanophenyl] ester
4-n-pentylbiphenyl-4'-carboxylic acid [4-(3-methylpentyl)-2-cyanophenyl] ester
4-n-pentylbiphenyl-4'-carboxylic acid (4-n-heptyl-2-cyanophenyl) ester, m.p. 50°; c.p. 101°;
4-n-pentylbiphenyl-4'-carboxylic acid (4-n-octyl-2-cyanophenyl) ester
4-n-pentylbiphenyl-4'-carboxylic acid [4-(2-ethylhexyl)-2-cyanophenyl] ester
4-n-pentylbiphenyl-4'-carboxylic acid (4-n-nonyl-2-cyanophenyl) ester
4-n-hexylbiphenyl-4'-carboxylic acid (4-n-propyl-2-cyanophenyl) ester
4-n-hexylbiphenyl-4'-carboxylic acid (4-n-butyl-2-cyanophenyl) ester
4-n-hexylbiphenyl-4'-carboxylic acid [4-(2-methylpropyl)-2-cyanophenyl] ester
4-n-hexylbiphenyl-4'-carboxylic acid (4-n-pentyl-2-cyanophenyl) ester
4-n-hexylbiphenyl-4'carboxylic acid [4-(2-methylbutyl)-2-cyanophenyl] ester
4-n-hexylbiphenyl-4'-carboxylic acid [4-(3-methylbutyl)-2-cyanophenyl] ester
4-n-hexylbiphenyl-4'-carboxylic acid (4-n-hexyl-2-cyanophenyl) ester
4-n-hexylbiphenyl-4'-carboxylic acid [4-(2-methylpentyl)-2-cyanophenyl] ester
4-n-hexylbiphenyl-4'-carboxylic acid [4-(3-methylpentyl)-2-cyanophenyl] ester
4-n-hexylbiphenyl-4'-carboxylic acid (4-n-heptyl-2-cyanophenyl) ester
4-n-hexylbiphenyl-4'-carboxylic acid (4-n-octyl-2-cyanophenyl) ester
4-n-hexylbiphenyl-4'-carboxylic acid [4-(2-ethylhexyl)-2-cyanophenyl] ester
4-n-heptylbiphenyl-4'-carboxylic acid (4-n-propyl-2-cyanophenyl) ester
4-n-heptylbiphenyl-4'-carboxylic acid (4-n-butyl-2-cyanophenyl) ester
4-n-heptylbiphenyl-4'-carboxylic acid [4-(2-methylpropyl)-2-cyanophenyl] ester
4-n-heptylbiphenyl-4'-carboxylic acid (4-n-pentyl-2-cyanophenyl) ester
4-n-heptylbiphenyl-4'-carboxylic acid [4-(2-methylbutyl)-2-cyanophenyl] ester
4-n-heptylbiphenyl-4'-carboxylic acid [4-(3-methylbutyl)-2-cyanophenyl] ester
4-n-heptylbiphenyl-4'-carboxylic acid (4-n-hexyl-2-cyanophenyl) ester
4-n-heptylbiphenyl-4'-carboxylic acid [4-(2-methylpentyl)-2-cyanophenyl] ester
4-n-heptylbiphenyl-4'-carboxylic acid [4-(3-methylpentyl)-2-cyanophenyl] ester
4-n-heptylbiphenyl-4'-carboxylic acid (4-n-heptyl-2-cyanophenyl) ester, m.p. 49°; c.p. 97°;
4-(2-methylpropyl)-biphenyl-4'-carboxylic acid (4-n-butyl-2-cyanophenyl) ester
4-(2-methylpropyl)-biphenyl-4'-carboxylic acid (4-n-pentyl-2-cyanophenyl) ester
4-(2-methylpropyl)-biphenyl-4'-carboxylic acid (4-n-hexyl-2-cyanophenyl) ester
4-(2-methylpropyl)-biphenyl-4'-carboxylic acid (4-n-heptyl-2-cyanophenyl) ester
4-(2-methylpropyl)-biphenyl-4'-carboxylic acid (4-n-octyl-2-cyanophenyl) ester
4-(2-methylpropyl)-biphenyl-4'-carboxylic acid (4-n-nonyl-2-cyanophenyl) ester
4-(2-methylbutyl)-biphenyl-4'-carboxylic acid (4-n-propyl-2-cyanophenyl) ester
4-(2-methylbutyl)-biphenyl-4'-carboxylic acid (4-n-butyl-2-cyanophenyl) ester
4-(2-methylbutyl)-biphenyl-4'-carboxylic acid (4-n-pentyl-2-cyanophenyl) ester
4-(2-methylbutyl)-biphenyl-4'-carboxylic acid (4-n-hexyl-2-cyanophenyl) ester
4-(2-methylbutyl)-biphenyl-4'-carboxylic acid (4-n-heptyl-2-cyanophenyl) ester
4-(2-methylbutyl)-biphenyl-4'-carboxylic acid (4-n-octyl-2-cyanophenyl) ester
4-(2-methylbutyl)-biphenyl-4'-carboxylic acid (4-n-nonyl-2-cyanophenyl) ester 4-(3-methylbutyl)-biphenyl-4'-carboxylic acid (4-n-propyl-2-cyanophenyl) ester
4-(3-methylbutyl)-biphenyl-4'-carboxylic acid (4-n-butyl-2-cyanophenyl) ester
4-(3-methylbutyl)-biphenyl-4'-carboxylic acid (4-n-pentyl-2-cyanophenyl) ester
4-(3-methylbutyl)-biphenyl-4'-carboxylic acid (4-n-hexyl-2-cyanophenyl) ester
4-(3-methylbutyl)-biphenyl-4'-carboxylic acid (4-n-heptyl-2-cyanophenyl) ester
4-(3-methylbutyl)-biphenyl-4'-carboxylic acid (4-n-octyl-2-cyanophenyl) ester
4-(3-methylbutyl)-biphenyl-4'-carboxylic acid (4-n-nonyl-2-cyanophenyl) ester
4-(2-methylpentyl)-biphenyl-4'-carboxylic acid (4-n-propyl-2-cyanophenyl) ester
4-(2-methylpentyl)-biphenyl-4'-carboxylic acid (4-n-butyl-2-cyanophenyl) ester
4-(2-methylpentyl)-biphenyl-4'-carboxylic acid (4-n-pentyl-2-cyanophenyl) ester
4-(2-methylpentyl)-biphenyl-4'-carboxylic acid (4-n-hexyl-2-cyanophenyl) ester
4-(2-methylpentyl)-biphenyl-4'-carboxylic acid (4-n-heptyl-2-cyanophenyl) ester
4-(2-methylpentyl)-biphenyl-4'-carboxylic acid (4-n-octyl-2-cyanophenyl) ester
4-(3-methylpentyl)-biphenyl-4'-carboxylic acid (4-n-propyl-2-cyanophenyl) ester
4-(3-methylpentyl)-biphenyl-4'-carboxylic acid (4-n-butyl-2-cyanophenyl) ester
4-(3-methylpentyl)-biphenyl-4'-carboxylic acid (4-n-pentyl-2-cyanophenyl) ester
4-(3-methylpentyl)-biphenyl-4'-carboxylic acid (4-n-hexyl-2-cyanophenyl) ester
4-(3-methylpentyl)-biphenyl-4'-carboxylic acid (4-n-heptyl-2-cyanophenyl) ester
4-(3-methylpentyl)-biphenyl-4'-carboxylic acid (4-n-octyl-2-cyanophenyl) ester
4-(2-ethylhexyl)-biphenyl-4'-carboxylic acid (4-n-propyl-2-cyanophenyl) ester
4-(2-ethylhexyl)-biphenyl-4'-carboxylic acid (4-n-butyl-2-cyanophenyl) ester
4-(2-ethylhexyl)-biphenyl-4'-carboxylic acid (4-n-pentyl-2-cyanophenyl) ester, m.p. 37°; c.p. 49.5°;
4-(2-ethylhexyl)-biphenyl-4'-carboxylic acid (4-n-hexyl-2-cyanophenyl) ester.

EXAMPLE 2

(a) At 15° under agitation, 33 g. of bromine is added dropwise during the course of 35 minutes to a solution of 50 g. of 4-n-pentyl-4'-hydroxybiphenyl in 300 ml. of chloroform. The mixture is then agitated for another 2 hours at room temperature, washed with 5% aqueous sodium bicarbonate solution and water, and dried over calcium chloride. Thereafter, the chloroform is removed by distillation and the remaining 4-n-pentyl-3'-bromo-4'-hydroxybiphenyl is recrystallized from methanol; yield: 61 g.

(b) 61 g. of 4-n-pentyl-3'-bromo-4'-hydroxybiphenyl is dissolved in 200 ml. of toluene and the solution is heated to boiling for 2 hours with 25 g. of acetic anhydride with the addition of 1 ml. of concentrated sulfuric acid. The reaction mixture is washed neutral with aqueous sodium bicarbonate solution, dried over sodium sulfate, and concentrated by evaporation. The remaining 4-n-pentyl-3'-bromo-4'-acetoxydiphenyl is recrystallized from ethanol; yield: 65.6 g.

(c) 65 g. of 4-n-pentyl-3'-bromo-4'-acetoxybiphenyl and 18 g. of copper(I) cyanide are heated in 360 ml. of a mixture of pyridine and N-methylpyrrolidone (2:1) for 2 hours at 160°. After cooling, a solution of 250 g. of ferric chloride hexahydrate in 1.2 l. of 20% hydrochloric acid is added to the reaction mixture, the latter is heated to 70° for 1.5 hours with agitation, and after cooling, extracted five times with 400 ml. portions of diethyl ether. The extracts are washed with aqueous sodium bicarbonate solution and water, dried over sodium sulfate, and evaporated. The remaining 4-n-pentyl-3'-cyano-4'-acetoxybiphenyl is recrystallized from ethanol; yield: 34 g.

(d) 34 g. of 4-n-pentyl-3'-cyano-4'-acetoxybiphenyl is heated for 30 minutes to boiling with 150 ml. of 10% aqueous potassium hydroxide solution. The mixture is then acidified with dilute hydrochloric acid. The thus-precipitated 4-n-pentyl-3'-cyano-4'-hydroxybiphenyl is filtered off and recrystallized from methanol; yield: 28.5 g.

(e) 26.5 g. of 4-n-pentyl-3'-cyano-4'-hydroxybiphenyl and 25 ml. of pyridine are dissolved in 250 ml. of toluene, and the solution is combined dropwise under agitation at 70°-80° with a solution of 22.5 g. of 4-n-hexylbenzoyl chloride in 100 ml. of toluene. The reaction mixture is then heated to boiling for 2 hours, filtered after cooling, and the filtrate is evaporated. The remaining [3-cyano-4'-n-pentylbiphenylyl-(4)] ester of 4-n-hexylbenzoic acid is recrystallized from ethanol; yield: 42.4 g.

Analogously, the following compounds are prepared:
4-n-pentylbenzoic acid [3-cyano-4'-n-propylbiphenylyl-(4)] ester
4-n-hexylbenzoic acid [3-cyano-4'-n-propylbiphenylyl-(4)] ester
4-n-heptylbenzoic acid [3-cyano-4'-n-propylbiphenylyl-(4)] ester
4-n-octylbenzoic acid [3-cyano-4'-n-propylbiphenylyl-(4)] ester
4-n-nonylbenzoic acid [3-cyano-4'-n-propylbiphenylyl-(4)] ester
4-(2-methylbutyl)-benzoic acid [3-cyano-4'-n-propylbiphenylyl-(4)] ester
4-(3-methylbutyl)-benzoic acid [3-cyano-4'-n-propylbiphenyl-(4)] ester
4-(2-methylpentyl)-benzoic acid [3-cyano-4'-n-propylbiphenylyl-(4)] ester
4-(3-methylpentyl)-benzoic acid [3-cyano-4'-n-propylbiphenylyl-(4)] ester
4-(2-ethylhexyl)-benzoic acid [3-cyano-4'-n-propylbiphenylyl-(4)] ester
4-n-butylbenzoic acid [3-cyano-4'-n-butylbiphenylyl-(4)] ester
4-n-pentylbenzoic acid [3-cyano-4'-n-butylbiphenylyl-(4)] ester
4-n-hexylbenzoic acid [3-cyano-4'-n-butylbiphenylyl-(4)] ester
4-n-heptylbenzoic acid [3-cyano-4'-n-butylbiphenylyl-(4)] ester
4-n-octylbenzoic acid [3-cyano-4'-n-butylbiphenylyl-(4)] ester
4-n-nonylbenzoic acid [3-cyano-4'-n-butylbiphenylyl-(4)] ester
4-(2-methylpropyl)-benzoic acid [3-cyano-4'-n-butylbiphenylyl-(4)] ester
4-(2-methylbutyl)-benzoic acid [3-cyano-4'-n-butylbiphenylyl-(4)] ester 4-(3-methylbutyl)-benzoic acid [3-cyano-4'-n-butyl-biphenylyl-(4)] ester
4-(2-methylpentyl)-benzoic acid [3-cyano-4'-n-butyl-biphenylyl-(4)] ester
4-(3-methylpentyl)-benzoic acid [3-cyano-4'-n-butyl-biphenylyl-(4)] ester
4-(2-ethylhexyl)-benzoic acid [3-cyano-4'-n-butyl-biphenylyl-(4)] ester
4-n-propylbenzoic acid [3-cyano-4'-n-pentylbiphenylyl-(4)] ester
4-n-butylbenzoic acid [3-cyano-4'-n-pentylbiphenylyl-(4)] ester
4-n-pentylbenzoic acid [3-cyano-4'-n-pentylbiphenylyl-(4)] ester
4-n-heptylbenzoic acid [3-cyano-4'-n-pentylbiphenylyl-(4)] ester
4-n-octylbenzoic acid [3-cyano-4'-n-pentylbiphenylyl-(4)] ester
4-n-nonylbenzoic acid [3-cyano-4'-n-pentylbiphenylyl-(4)] ester
4-(2-methylpropyl)-benzoic acid [3-cyano-4'-n-pentylbiphenylyl-(4)] ester
4-(2-methylbutyl)-benzoic acid [3-cyano-4'-n-pentylbiphenylyl-(4)] ester
4-(3-methylbutyl)-benzoic acid [3-cyano-4'-n-pentylbiphenylyl-(4)] ester
4-(2-methylpentyl)-benzoic acid [3-cyano-4'-n-pentylbiphenylyl-(4)] ester
4-(3-methylpentyl)-benzoic acid [3-cyano-4'-n-pentylbiphenylyl-(4)] ester
4-(2-ethylhexyl)-benzoic acid [3-cyano-4'-n-pentylbiphenylyl-(4)] ester
4-n-propylbenzoic acid [3-cyano-4'-n-hexylbiphenylyl-(4)] ester
4-n-butylbenzoic acid [3-cyano-4'-n-hexylbiphenylyl-(4)] ester
4-n-pentylbenzoic acid[3-cyano-4'-n-hexylbiphenylyl-(4)] ester
4-n-hexylbenzoic acid [3-cyano-4'-n-hexylbiphenylyl-(4)] ester
4-n-heptylbenzoic acid [3-cyano-4'-n-hexylbiphenylyl-(4)] ester
4-n-octylbenzoic acid [3-cyano-4'-n-hexylbiphenylyl-(4)] ester
4-(2-methylpropyl)-benzoic acid [3-cyano-4'-n-hexylbiphenylyl-(4)] ester
4-(2-methylbutyl)-benzoic acid [3-xyano-4'-n-hexylbiphenylyl-(4)] ester
4-(3-methylbutyl)-benzoic acid [3-cyano-4'-n-hexylbiphenylyl-(4)] ester
4-(2-methylpentyl)-benzoic acid [3-cyano-4'-n-hexylbiphenylyl-(4)] ester
4-(3-methylpentyl)-benzoic acid [3-cyano-4'-n-hexylbiphenylyl-(4)] ester
4-(2-ethylhexyl)-benzoic acid [3-cyano-4'-n-hexylbiphenylyl-(4)] ester
4-n-propylbenzoic acid [3-cyano-4'-n-heptylbiphenylyl-(4)] ester
4-n-butylbenzoic acid [3-cyano-4'-n-heptylbiphenylyl-(4)] ester
4-n-pentylbenzoic acid [3-cyano-4'-n-heptylbiphenylyl-(4)] ester
4-n-hexylbenzoic acid [3-cyano-4'-n-heptylbiphenylyl-(4)] ester
4-n-heptylbenzoic acid [3-cyano-4'-n-heptylbiphenylyl-(4)] ester
4-(2-methylpropyl)-benzoic acid [3-cyano-4'-n-heptylbiphenylyl-(4)] ester
4-(2-methylbutyl)-benzoic acid [3-cyano-4'-n-heptylbiphenylyl-(4)] ester
4-(3-methylbutyl)-benzoic acid [3-cyano-4'-n-heptylbiphenylyl-(4)] ester
4-(2-methylpentyl)-benzoic acid [3-cyano-4'-n-heptylbiphenylyl-(4)] ester
4-(3-methylpentyl)-benzoic acid [3-cyano-4'-n-heptylbiphenylyl-(4)] ester
4-n-butylbenzoic acid [3-cyano-4'-(2-methylpropyl)-biphenylyl-(4)] ester
4-n-pentylbenzoic acid [3-cyano-4'-(2-methylpropyl)-biphenylyl-(4)] ester
4-n-hexylbenzoic acid [3-cyano-4'-(2-methylpropyl)-biphenylyl-(4)] ester
4-n-heptylbenzoic acid [3-cyano-4'-(2-methylpropyl)-biphenylyl-(4)] ester
4-n-octylbenzoic acid [3-cyano-4'-(2-methylpropyl)-biphenylyl-(4)] ester
4-n-nonylbenzoic acid [3-cyano-4'-(2-methylpropyl)-biphenylyl-(4)] ester
4-n-propylbenzoic acid [3-cyano-4'-(2-methylbutyl)-biphenylyl-(4)] ester
4-n-butylbenzoic acid [3-cyano-4'-(2-methylbutyl)-biphenylyl-(4)] ester
4-n-pentylbenzoic acid [3-cyano-4'-(2-methybutyl)-biphenylyl-(4)] ester
4-n-hexylbenzoic acid [3-cyano-4'-(2-methylbutyl)-biphenylyl-(4)] ester
4-n-heptylbenzoic acid [3-cyano-4'-(2-methylbutyl)-biphenylyl-(4)] ester
4-n-octylbenzoic acid [3-cyano-4'-(2-methylbutyl)-biphenylyl-(4)] ester
4-n-nonylbenzoic acid [3-cyano-4'-(2-methylbutyl)-biphenylyl-(4)] ester
4-n-propylbenzoic acid [3-cyano-4'-(3-methylbutyl)-biphenylyl-(4)] ester
4-n-butylbenzoic acid [3-cyano-4'-(3-methylbutyl)-biphenylyl-(4)] ester
4-pentylbenzoic acid [3-cyano-4'-(3-methylbutyl)-biphenylyl-(4)] ester
4-n-hexylbenzoic acid [3-cyano-4'-(3-methylbutyl)-biphenylyl-(4)] ester
4-n-heptylbenzoic acid [3-cyano-4'-(3-methylbutyl)-biphenylyl-(4)] ester
4-n-octylbenzoic acid [3-cyano-4'-(3-methylbutyl)-biphenylyl-(4)] ester
4-n-nonylbenzoic acid [3-cyano-4'-(3-methylbutyl)-biphenylyl-(4)] ester
4-n-propylbenzoic acid [3-cyano-4'-(2-methylpentyl)-biphenylyl-(4)] ester
4-n-butylbenzoic acid [3-cyano-4'-(2-methylpentyl)-biphenylyl-(4)] ester
4-n-pentylbenzoic acid [3-cyano-4'-(2-methylpentyl)-biphenylyl-(4)] ester
4-n-hexylbenzoic acid [3-cyano-4'-(2-methylpentyl)-biphenylyl-(4)] ester
4-n-heptylbenzoic acid [3-cyano-4'-(2-methylpentyl)-biphenylyl-(4)] ester
4-n-octylbenzoic acid [3-cyano-4'-(2-methylpentyl)-biphenylyl-(4)] ester
4-n-propylbenzoic acid [3-cyano-4'-(3-methylpentyl)-biphenylyl-(4)] ester
4-n-butylbenzoic acid [3-cyano-4'-(3-methylpentyl)-biphenylyl-(4)] ester
4-n-pentylbenzoic acid [3-cyano-4'-(3-methylpentyl)-biphenylyl-(4)] ester
4-n-hexylbenzoic acid [3-cyano-4'-(3-methylpentyl)-biphenylyl-(4)] ester 4-n-heptylbenzoic acid [3-cyano-4'-(3-methylpentyl)-biphenylyl-(4)] ester 4-n-octylbenzoic acid [3-cyano-4'-(3-methylpentyl)-biphenylyl-(4)] ester 4-n-propylbenzoic acid [3-cyano-4'-(2-ethylhexyl)-biphenylyl-(4)] ester 4-n-butylbenzoic acid [3-cyano-4'-(2-ethylhexyl)-biphenylyl-(4)] ester 4-n-pentylbenzoic acid [3-cyano-4'-(2-ethylhexyl)-biphenylyl-(4)] ester 4-n-hexylbenzoic acid [3-cyano-4'-(2-ethylhexyl)-biphenylyl-(4)] ester.

In the examples set forth below for dielectrics according to this invention, the additives consisting of doping agents for affecting the conductivity, the orientation, and/or for the chemical or photochemical stabilization, which are not essential to the invention, have not been included for the sake of clarity. Such doping agents can be added to the indicated mixtures in correspondence with a specific problem without there being an essential change in the electrooptical properties of these mixtures. The data regarding the composition of the dielectrics of the present invention are in percent by weight.

EXAMPLE 3

A liquid crystalline mixture of 66% anisic acid 4-n-pentylphenyl ester and 34% 4-n-hexyloxybenzoic acid 4'-n-pentylphenyl ester has a clearing point of 49°, a viscosity of 60 cp., and a DA value of +0.1. A dielectric made up of 90% of this mixture and 10% of a compound of this invention, 4-n-pentylbiphenyl-4'-carboxylic acid (4-n-butyl-2-cyanophenyl) ester has a clearing point of 54°, a viscosity of 72 cp., and a DA value of −0.25. In contrast thereto, a dielectric made up of 90% of the aforementioned liquid crystalline ester mixture and 10% of 4-(4-n-hexyloxybenzoyloxy)-benzoic acid (2-cyano-4-n-butylphenyl) ester has, with the same DA value, a clearing point of 56° and a viscosity of 92 cp. The dielectric of this invention thus is more suitable for use in a liquid crystal display device operating on the basis of the effect of dynamic scattering effect.

EXAMPLE 4

A dielectric of 80% of the liquid crystalline ester mixture described in Example 3 and 20% 4-n-pentyl-biphenyl-(4')-carboxylic acid (4-n-butyl-2-cyanophenyl) ester has a clearing point of 59° and a DA value of −0.6.

EXAMPLE 5

A liquid crystalline mixture of 45% 4-n-butyl-4'-methoxyazoxybenzene, 25% 4-ethyl-4'-methoxyazoxybenzene, 15% 4-n-pentylbiphenyl-(4')-carboxylic acid (4-n-pentylphenyl) ester and 15% 4-n-pentylbiphenyl-(4')-carboxylic acid (4-n-butylphenyl) ester has a clearing point of 106° and a DA value of +0.04. A dielectric of 90% of this mixture and 10% of the compound according to this invention, 4-n-pentylbiphenyl-(4')-carboxylic acid (2-cyano-4-n-butylphenyl) ester, has a clearing point of 107° and a DA value of −0.37. A dielectric of 85% of the above-described mixture and 15% of the just mentioned compound of this invention has a clearing point of 107.5° and a DA value of −0.55.

EXAMPLE 6

A dielectric of 60% 4-n-butyl-4'-methoxyazoxybenzene, 30% 4-ethyl-4'-methoxyazoxybenzene, and 10% 4-n-heptylbenzoic acid [3-cyano-4'-n-pentylbiphenylyl-(4)] ester has a clearing point of 76° and a DA value of −0.6.

EXAMPLE 7

A dielectric of 61.6% 4-n-butyl-4'-methoxyazoxybenzene, 30.4% 4-ethyl-4'-methoxyazoxybenzene, and 8% 4-n-pentylbiphenyl-(4')-carboxylic acid (2-cyano-4-n-heptylphenyl) ester is nematic in a temperature range of −4° to +78° and has a DA value of −0.55 and a viscosity of 38 cp.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A biphenyl compound of the formula

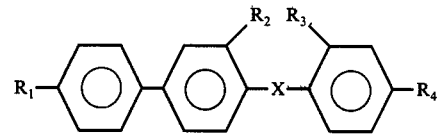

wherein X is —CO—O or —O—CO, $R_1$ and $R_4$ are alkyl of 1-10 carbon atoms, and wherein $R_2$ is CN and $R_3$ is hydrogen when X is —O—CO and $R_3$ is CN and $R_2$ is hydrogen when X is —CO—O.

2. A compound of claim 1, of the formula

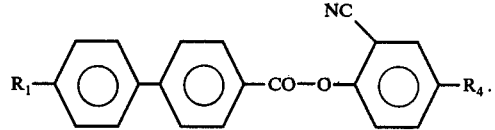

3. A compound of claim 1, of the formula

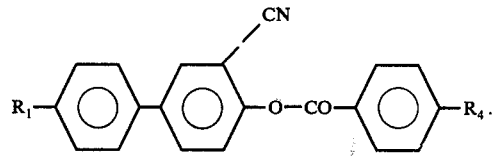

4. A compound of claim 1, selected from the group consisting of:

4-n-propylbiphenyl-(4')-carboxylic acid (2-cyano-4-n-pentylphenyl) ester, 4-n-propylbiphenyl-(4')-carboxylic acid (2-cyano-4-n-heptylphenyl) ester, 4-n-pentylbiphenyl-(4')-carboxylic acid (2-cyano-4-n-butylphenyl) ester, 4-n-pentylbiphenyl-(4')-carboxylic acid (2-cyano-4-n-pentylphenyl) ester, 4-n-pentylbiphenyl-(4')-carboxylic acid (2-cyano-4-n-heptylphenyl) ester, 4-n-pentylbiphenyl-(4')-carboxylic acid (2-cyano-4-n-nonylphenyl) ester, and 4-n-heptylbiphenyl-(4')-carboxylic acid (2-cyano-4-n-heptylphenyl) ester.

5. A compound of claim 1, selected from the group consisting of:
4-n-pentylbenzoic acid [3-cyano-4'-n-butylbiphenylyl-(4)] ester,
4-n-pentylbenzoic acid [3-cyano-4'-n-pentylbiphenylyl-(4)] ester,
4-n-pentylbenzoic acid [3-cyano-4'-n-hexylbiphenylyl-(4)] ester,
4-n-pentylbenzoic acid [3-cyano-4'-n-heptylbiphenylyl-(4)] ester,
4-n-hexylbenzoic acid [3-cyano-4'-n-butylbiphenylyl-(4)] ester,
4-n-hexylbenzoic acid [3-cyano-4'-n-pentylbiphenylyl-(4)] ester,
4-n-hexylbenzoic acid [3-cyano-4'-n-hexylbiphenylyl-(4)] ester, and
4-n-butylbenzoic acid [3-cyano-4'-(2-methylpentyl)-biphenylyl-(4)] ester.

6. In a liquid crystalline dielectric composition having a negative dielectric anisotropy and comprising at least one liquid crystalline compound free of —CN, —NC and $NO_2$ radicals, the improvement wherein the composition contains 0.5–40% by weight of a compound of claim 1.

7. In a liquid crystalline dielectric composition having a negative dielectric anisotropy and comprising at least one liquid crystalline compound free of —CN, —NC and $NO_2$ radicals, the improvement wherein the composition contains 1–35% by weight of a compound of claim 1.

8. In a liquid crystalline dielectric composition having a negative dielectric anisotropy and comprising at least one liquid crystalline compound free of —CN, —NC and $NO_2$ radicals, the improvement wherein the composition contains 5–30% by weight of a compound of claim 1.

9. In a liquid crystalline dielectric composition having a negative dielectric anisotropy and comprising at least one liquid crystalline compound free of —CN, —NC and $NO_2$ radicals, the improvement wherein the composition contains 0.5–40% by weight of a compound of claim 2.

10. In a liquid crystalline dielectric composition having a negative dielectric anisotropy and comprising at least one liquid crystalline compound free of —CN, —NC and $NO_2$ radicals, the improvement wherein the composition contains 0.5–40% by weight of a compound of claim 3.

* * * * *